United States Patent
Ishizuka et al.

(10) Patent No.: US 10,639,244 B2
(45) Date of Patent: May 5, 2020

(54) DENTAL PHOTOPOLYMERIZABLE COMPOSITION AND PHOTOPOLYMERIZATION INITIATOR

(71) Applicant: GC Corporation, Shizuoka (JP)

(72) Inventors: So Ishizuka, Tokyo (JP); Yusuke Sakaguchi, Tokyo (JP); Naofumi Matsumoto, Tokyo (JP)

(73) Assignee: GC Corporation, Shizuoka (JP)

( * ) Notice: Subject to any disclaimer, the term of this patent is extended or adjusted under 35 U.S.C. 154(b) by 0 days.

(21) Appl. No.: 16/175,973

(22) Filed: Oct. 31, 2018

(65) Prior Publication Data

US 2019/0142704 A1 May 16, 2019

(30) Foreign Application Priority Data

Nov. 14, 2017 (JP) .................. 2017-218804

(51) Int. Cl.
| | | |
|---|---|---|
| C08F 2/46 | (2006.01) |
| C08F 2/50 | (2006.01) |
| C08G 61/04 | (2006.01) |
| A61K 6/887 | (2020.01) |
| C08F 222/10 | (2006.01) |
| A61C 5/77 | (2017.01) |
| A61C 13/15 | (2006.01) |
| A61K 6/62 | (2020.01) |
| A61K 6/80 | (2020.01) |
| A61K 6/824 | (2020.01) |

(52) U.S. Cl.
CPC ............... *A61K 6/887* (2020.01); *A61C 5/77* (2017.02); *A61C 19/003* (2013.01); *A61K 6/62* (2020.01); *A61K 6/80* (2020.01); *A61K 6/824* (2020.01); *C08F 222/1006* (2013.01); *C08F 222/102* (2020.02); *C08F 2800/20* (2013.01)

(58) Field of Classification Search
USPC ............. 522/28, 7, 6, 189, 184, 1, 71; 520/1
See application file for complete search history.

(56) References Cited

U.S. PATENT DOCUMENTS

| | | | |
|---|---|---|---|
| 6,300,389 B1 | 10/2001 | Sato et al. | |
| 2005/0009946 A1* | 1/2005 | Oguri | A61K 6/0023 522/184 |
| 2010/0311864 A1 | 12/2010 | Arita et al. | |
| 2011/0124763 A1* | 5/2011 | Hinamoto | A61K 6/0052 522/28 |
| 2011/0172323 A1* | 7/2011 | Akizumi | A61K 6/0052 522/25 |
| 2014/0329205 A1* | 11/2014 | Hecht | C09J 175/16 433/228.1 |
| 2016/0051450 A1 | 2/2016 | Kashiki et al. | |

FOREIGN PATENT DOCUMENTS

JP H11-209214 8/1999

\* cited by examiner

*Primary Examiner* — Jessica Whiteley
(74) *Attorney, Agent, or Firm* — IPUSA, PLLC

(57) ABSTRACT

A single-component dental photopolymerizable composition is provided that includes a (meth)acrylate compound, a vanadium compound, an α-diketone compound, and a tertiary aromatic amine compound.

9 Claims, No Drawings

DENTAL PHOTOPOLYMERIZABLE COMPOSITION AND PHOTOPOLYMERIZATION INITIATOR

CROSS-REFERENCE TO RELATED APPLICATION

The present application is based on and claims priority to Japanese Patent Application No. 2017-218804 filed on Nov. 14, 2017, the entire contents of which are hereby incorporated by reference.

BACKGROUND OF THE INVENTION

1. Field of the Invention

The present invention generally relates to a dental photopolymerizable composition and a photopolymerization initiator.

2. Description of the Related Art

When fixing a dental prosthesis to a remaining tooth, if the remaining tooth structure is substantially whole, a technician cuts the remaining tooth structure into a shape approximating a truncated cone shape using a turbine and uses the remaining tooth that has been cut as an abutment tooth.

On the other hand, when fixing a dental prosthesis to a remaining tooth, if the remaining tooth is substantially damaged such that only the tooth root remains, a technician inserts a fiber post into the root canal and thereafter constructs a fiber core using a composite resin for abutment construction. Thereafter, the technician cuts the fiber core into a shape approximating a truncated cone shape using a turbine and uses the cut fiber core as an abutment tooth.

The composite resin for abutment construction is typically a photopolymerizable composition in the form of a paste that facilitates construction of an abutment. The composite resin for abutment construction can be hardened (set) by irradiating sufficient light onto the composite resin for abutment construction.

An example of the composite resin for abutment construction includes a so-called dual-cure composite resin for abutment construction that has both a chemical-curing component (that sets by chemical polymerization) and a light-curing component (that sets by polymerization).

However, because a dual-cure composite resin for abutment construction has two components, it imposes the burden of mixing the two components together.

On the other hand, a single-component composite resin for abutment construction is described, for example, in Japanese Unexamined Patent Publication No. H11-209214.

However, because a single-component composite resin for abutment construction only sets by photopolymerization, a smaller amount of radicals are generated during the setting time of the single-component composite resin as compared with a two-component composite resin that utilizes both setting by chemical polymerization and setting by photopolymerization. As such, the set product resulting from setting the single-component composite resin may have a lower elastic modulus as compared with the set product of a two-component composite resin.

Note that a set product of a composite resin for abutment construction is preferably arranged to have an elastic modulus that is as close as possible to a range from 12 GPa to 19 GPa corresponding to the elastic modulus of human dentin.

SUMMARY OF THE INVENTION

One aspect of the present invention is directed to providing a single-component dental photopolymerizable composition that can be used to produce a set product having a desirably high elastic modulus.

According to one embodiment of the present invention, a single-component dental photopolymerizable composition is provided that includes a (meth)acrylate compound, a vanadium compound, an α-diketone compound, and a tertiary aromatic amine compound.

DESCRIPTION OF THE PREFERRED EMBODIMENTS

In the following, embodiments for implementing the present invention will be described.

A dental photopolymerizable composition according to an embodiment of the present invention is a one-component system and includes a (meth)acrylate compound, a vanadium compound, an α-diketone compound, and a tertiary aromatic amine compound. According to an aspect of the present embodiment, the amount of radicals generated during the setting time of the dental photopolymerizable composition may be increased, and the elastic modulus of the set product of the dental photopolymerizable composition may be increased.

Examples of the vanadium compound include, but are not limited to, vanadium acetylacetonate, vanadyl acetylacetonate, vanadyl stearate, vanadium naphthenate, vanadium benzoylacetonate, and the like, as well as a combination of two or more of the above-noted substances. Note that among the above-noted substances, vanadium acetylacetonate and vanadyl acetylacetonate are particularly suitable.

The content of the vanadium compound in the dental photopolymerizable composition according to the present embodiment is preferably greater than or equal to 0.001 mass % and less than or equal to 1 mass %, and more preferably greater than or equal to 0.005 mass % and less than or equal to 0.2 mass %. When the content of the vanadium compound in the dental photopolymerizable composition according to the present embodiment is greater than or equal to 0.001 mass %, the elastic modulus of the set product of the dental photopolymerizable composition may be increased, and when content of the vanadium compound in the dental photopolymerizable composition according to the present embodiment is less than or equal to 1 mass %, the storage stability of the dental photopolymerizable composition may be improved.

Examples of the α-diketone compound include, but are not limited to, camphorquinones such as camphorquinone, camphorquinone carboxylic acid, camphorquinone sulfonic acid, and the like; benzyl; diacetyl; dibenzyl; acetylbenzoyl; 2,3-pentadione; 2,3-octadione; 9,10-phenanthrenequinone; 4,4'-oxybenzyl; acenaphthenequinone; and a combination of two or more of the above-noted substances. Note that among the above-noted substances, camphorquinone is particularly suitable.

The content of the α-diketone compound in the dental photopolymerizable composition according to the present embodiment is preferably greater than or equal to 0.01 mass % and less than or equal to 1 mass %, and more preferably greater than or equal to 0.05 mass % and less than or equal to 0.5 mass %. When the content of the α-diketone compound in the dental photopolymerizable composition according to the present embodiment is greater than or equal to 0.01 mass %, the elastic modulus of the set product of the dental photopolymerizable composition may be increased, and when the content of the α-diketone compound in the dental photopolymerizable composition according to the present embodiment is less than or equal to 1 mass %, the stability of the dental photopolymerizable composition to ambient light may be improved.

The tertiary aromatic amine compound preferably has an alkyloxycarbonyl group coupled at the para position. In this way, the elastic modulus of the set product of the dental photopolymerizable composition may be increased.

Examples of the tertiary aromatic amine compound having an alkyloxycarbonyl group coupled at the para position include, but is not limited to, p-dimethylaminobenzoic acid methyl ester, p-dimethylaminobenzoic acid ethyl ester, p-dimethylaminobenzoic acid propyl ester, p-dimethylaminobenzoic acid amyl ester, p-dimethylaminobenzoic acid isoamyl ester, p-diethylaminobenzoic acid ethyl ester, p-diethylaminobenzoic acid propyl ester, and the like.

Examples of the tertiary aromatic amine compound other than those mentioned above include, but are not limited to, N,N-dimethylaniline, N,N-dibenzylaniline, N,N-dimethyl-p-toluidine, N,N-diethyl-p-toluidine, N,N-bis(β-hydroxyethyl)-p-toluidine, N,N,2,4,6-pentamethylaniline, N,N,2,4-tetramethylaniline, N,N-diethyl-2,4,6-trimethylaniline, and the like.

Note that in some embodiments of the present invention, two or more types of tertiary aromatic amine compounds may be used in combination.

The content of the tertiary aromatic amine compound in the dental photopolymerizable composition according to the present embodiment is preferably greater than or equal to 0.01 mass % and less than or equal to 5 mass %, and more preferably greater than or equal to 0.2 mass % and less than or equal to 2 mass %. When the content of the tertiary aromatic amine compound in the dental photopolymerizable composition according to the present embodiment is greater than or equal to 0.01 mass %, the elastic modulus of the set product of the dental photopolymerizable composition may be increased, and when the content of the tertiary aromatic amine compound in the dental photopolymerizable composition according to the present embodiment is less than or equal to 5 mass %, the storage stability of the dental photopolymerizable composition may be improved.

The (meth)acrylate compound may be either a monomer or an oligomer, but is preferably a monomer.

Examples of the (meth)acrylate monomer include, but are not limited to, methyl (meth)acrylate, ethyl (meth)acrylate, isopropyl (meth)acrylate, 2-hydroxyethyl (meth)acrylate, 2-hydroxypropyl (meth)acrylate, 2-hydroxy-1,3-di(meth)acryloxy propane, n-butyl (meth)acrylate, isobutyl (meth)acrylate, butoxyethyl (meth)acrylate, hydroxypropyl (meth)acrylate, tetrahydrofurfuryl (meth)acrylate, glycidyl (meth)acrylate, 2-methoxyethyl (meth)acrylate, 2-ethylhexyl (meth)acrylate, benzyl (meth)acrylate, ethylene glycol di(meth)acrylate, diethylene glycol (meth)acrylate, triethylene glycol di(meth)acrylate, triethylene glycol tri(meth)acrylate, butylene glycol di(meth)acrylate, neopentyl glycol di(meth)acrylate, 1,3-butanediol di(meth)acrylate, 1,4-butanediol di(meth)acrylate, 1,6-hexanediol di(meth)acrylate, trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, polyoxytetraethylene glycol di(meth)acrylate, 2,2-bis{(meth)acryloxyphenyl}propane, 2,2-bis[4-{2-hydroxy-3-(meth)acryloxypropoxy}phenyl]propane, 2,2-bis{4-(meth)acryloxydiethoxyphenyl}propane, 2,2-bis{4-(meth)acryloxypolyethoxyphenyl}propane, bisphenol A diglycidyl (meth)acrylate, urethane bond-containing (meth)acrylates such as di-2-(meth)acryloxyethyl-2,2,4-trimethylhexamethylenedicarbamate, 1,3,5-tris[1,3-bis{(meth)acryloyloxy}-2-propoxycarbonylaminohexane]-1,3,5-(1H,3H,5H)triazine-2,4,6-trione, and the like, as well as a combination of two or more of the above-noted substances.

The content of the (meth)acrylate compound in the dental photopolymerizable composition according to the present embodiment is preferably greater than or equal to 10 mass % and less than or equal to 90 mass %, and more preferably greater than or equal to 20 mass % and less than or equal to 50 mass %. When the content of the (meth)acrylate compound in the dental photopolymerizable composition is greater than or equal to 10 mass % and less than or equal to 90 mass %, operability of the dental photopolymerizable composition may be improved.

The dental photopolymerizable composition according to the present embodiment preferably further includes a filler. By including a filer in the dental photopolymerizable composition, the mechanical strength of the set product of the dental photopolymerizable composition may be improved.

Example materials of the filler include, but are not limited to, glass containing alkaline earth metal atoms such as anhydrous silicic acid, calcium glass, strontium glass, and barium glass; glass such as zinc glass, lead glass, alumina glass, potassium glass, and fluoroaluminosilicate glass; synthetic zeolite, calcium phosphate, feldspar, colloidal silica, fumed silica, aluminum silicate, calcium silicate, magnesium carbonate, hydrated silicic acid, hydrated calcium silicate, hydrated aluminum silicate, quartz, and the like.

Because the dental photopolymerizable composition according to the present embodiment contains a (meth)acrylate compound, the filler used in the dental photopolymerizable composition is preferably a hydrophobic filler that is surface-treated with a silane coupling agent including a vinyl group so that the filler would bond with the (meth)acrylate compound.

Examples of the silane coupling agent including a vinyl group include, but is not limited to, γ-(meth)acryloyloxypropyltrimethoxysilane, vinyltrichlorosilane, vinyltriethoxysilane, vinyltrimethoxysilane, vinyltriacetoxysilane, vinyltris(2-methoxyethoxy)silane, and the like.

The filler may also be an organic/inorganic composite filler prepared by mixing monomer(s) and/or oligomer(s) of the above (meth)acrylate compound, setting the mixture, and pulverizing the mixture.

Note that the above examples of the filler may be used alone or in combination.

The content of the filler in the dental photopolymerizable composition according to the present embodiment can be suitably selected depending on the application, the required mechanical strength of the dental photopolymerizable composition, and the like. However, the content of the filler in the dental photopolymerizable composition according to the present embodiment is preferably greater than or equal to 10 mass % and less than or equal to 90 mass %, and more preferably greater than or equal to 30 mass % and less than or equal to 80 mass %. When the content of the filler in the dental photopolymerizable composition is greater than or equal to 10 mass % and less than or equal to 90 mass %, the elastic modulus of the set product of the dental photopolymerizable composition may be increased.

The median diameter of the filler is not particularly limited, but it is preferably greater than or equal to 0.001 μm and less than or equal to 100 μm, and more preferably greater than or equal to 0.01 μm and less than or equal to 10 μm. When the median diameter of the filler is greater than or equal to 0.001 μm and less than or equal to 100 μm, operability of the dental photopolymerizable composition may be improved.

Note that median diameter means the particle diameter at 50% in the cumulative distribution of the number-based particle size distribution determined using the laser diffraction/scattering method.

The dental photopolymerizable composition according to the present embodiment may further contain a polymerization inhibitor such as 2,6-di-tert-butyl-p-cresol, and a photopolymerization initiator such as 2,4,6-trimethylbenzoyldiphenylacylphosphine oxide, for example.

The dental photopolymerizable composition according to the present embodiment may be used as a composite resin for abutment construction, a composite resin for filling, and the like.

EXAMPLES

In the following, the present invention will be described in detail with reference to examples and comparative examples. Note, however, that the present invention is not limited to these examples.

Examples 1 to 10, Comparative Examples 1 to 3

In the examples and comparative examples, first, liquid samples were prepared by mixing the listed materials at the mix ratios [parts by mass] indicated in Tables 1 and 2 below. Note that Lucirin TPO is 2,4,6-trimethylbenzoyldiphenylacylphosphine oxide.

Then, paste (photopolymerizable composition) samples were obtained by mixing each of the liquid samples with inorganic fillers at the mix ratios [mass %] indicated in Tables 1 and 2.

Note that hydrophobic silica is silica that has a median diameter of 1 μm and has been surface-treated with a silane coupling agent including a vinyl group. The hydrophobic silica was prepared by mixing 100 parts by mass of silica having a median diameter of 1 μm, 10 parts by mass of ethanol, and 3 parts by mass of methacryloyloxyoctyltrimethoxysilane using a dry method and heat treating the mixture.

Note that AEROSIL OX 50 and AEROSIL A200 (manufactured by Nippon Aerosil Co., Ltd.) are hydrophilic fumed silica.

Then, the bending strength and the elastic modulus of the set products of the paste samples, and the extrusion hardness of the paste samples were evaluated.

<Bending Strength and Bending Elastic Modulus>

Each paste sample was pressed into a mold having a 2×2×25 [mm] through hole via cellophane by two slide glasses. Then, using a visible light irradiator, G-Light Prima (manufactured by GC Corporation), visible light was irradiated for 10 seconds with the circular irradiation window of the irradiator pressed against one slide glass at the center of the mold. Then, the irradiation window was moved from the portion irradiated immediately before by half the diameter of the irradiation window and visible light was irradiated for 10 seconds. Further, the irradiation window was moved from the initially irradiated portion by half the diameter of the irradiation window in the opposite direction (direction opposite the immediately preceding moving direction) with respect to the center of the mold and visible light was irradiated for 10 seconds. The above procedure was repeated until the entire length of the paste in the mold was irradiated with visible light. Further, the above-described procedure for irradiating visible light was similarly performed with respect to the other slide glass.

After removing the test sample from the mold, burrs were removed using waterproof abrasive paper. Then, the test sample was immersed in distilled water at 37° C. for 24 hours and then subjected to a three-point bending test using a universal testing machine, Autograph (manufactured by Shimadzu Corporation), with a span of 20 mm and at a crosshead speed of 1 mm/min, to measure the bending strength and the bending elastic modulus of the test sample.

Note that the paste sample was deemed to be acceptable if the bending strength of the set product of the paste sample was greater than or equal to 170 MPa.

Also, the paste sample was deemed to be acceptable if the bending elastic modulus of the set product of the paste sample was greater than or equal to 10 GPa.

<Extrusion Hardness>

4 g of each paste sample was filled into a syringe container of a syringe, MI FIL (manufactured by GC Corporation). After fitting Dispensing Tip III Plastic (manufactured by GC Corporation) to the tip of the syringe, a piston was pushed into the syringe using the universal testing machine, Autograph (manufactured by Shimadzu Corporation), at a crosshead speed of 10 mm/min, to measure the extrusion hardness of the paste sample. Note that the paste sample was deemed to be acceptable if the extrusion hardness of the paste sample was less than or equal to 30 N.

The evaluation results of the bending strength and the elastic modulus of the set products of the paste samples and the extrusion hardness of the paste samples are indicated in Tables 1 and 2.

TABLE 1

| | EXAMPLE | | | | | |
|---|---|---|---|---|---|---|
| | 1 | 2 | 3 | 4 | 5 | 6 |
| LIQUID | | | | | | |
| GLYCERIN DIMETHACRYLATE | 30 | 30 | 30 | 30 | 30 | 30 |
| URETHANE DIMETHACRYLATE | 70 | 70 | 70 | 70 | 70 | 60 |
| ETHOXYLATED BISPHENOL A DIMETHACRYLATE | | | | | | 10 |
| p-(DIMETHYLAMINO) BENZOIC ACID ETHYL ESTER | 1.2 | 1.2 | 1.2 | 1.2 | 1.2 | 1.2 |
| 2,6-DI-TERT-BUTYL-p-CRESOL | 0.20 | 0.20 | 0.20 | 0.20 | 0.20 | 0.20 |

TABLE 1-continued

|  | EXAMPLE | | | | | |
| --- | --- | --- | --- | --- | --- | --- |
|  | 1 | 2 | 3 | 4 | 5 | 6 |
| LUCIRIN TPO | 0.10 | 0.10 | 0.10 | 0.10 | 0.10 | 0.10 |
| CAMPHORQUINONE | 0.2 | 0.2 | 0.2 | 0.2 | 0.2 | 0.5 |
| VANADYL ACETYLACETONATE | 0.20 | 0.10 | 0.06 | 0.04 | 0.02 | 0.06 |
| TOTAL | 101.90 | 101.80 | 101.76 | 101.74 | 101.72 | 102.06 |
| PASTE | | | | | | |
| LIQUID | 25 | 25 | 25 | 25 | 25 | 26 |
| HYDROPHOBIC SILICA | 74 | 74 | 74 | 74 | 74 | 71 |
| AEROSIL OX-50 |  |  |  |  |  | 3 |
| AEROSIL A200 | 1 | 1 | 1 | 1 | 1 |  |
| TOTAL | 100 | 100 | 100 | 100 | 100 | 100 |
| EVALUATION RESULT | | | | | | |
| BENDING STRENGTH [MPa] | 182 | 187 | 190 | 197 | 180 | 183 |
| ELASTIC MODULUS [GPa] | 11.1 | 11.1 | 11.1 | 10.8 | 10.5 | 11.2 |
| EXTRUSION HARDNESS [N] | 19.4 | 19.8 | 20.5 | 19.0 | 20.1 | 9.6 |

TABLE 2

|  | EXAMPLE | | | | COMPARATIVE EXAMPLE | | |
| --- | --- | --- | --- | --- | --- | --- | --- |
|  | 7 | 8 | 9 | 10 | 1 | 2 | 3 |
| LIQUID | | | | | | | |
| GLYCERIN DIMETHACRYLATE | 30 | 30 | 30 | 30 | 30 | 30 | 30 |
| URETHANE DIMETHACRYLATE | 60 | 60 | 70 | 70 | 70 | 60 | 60 |
| ETHOXYLATED BISPHENOL A DIMETHACRYLATE | 10 | 10 |  |  |  | 10 | 10 |
| p-(DIMETHYLAMINO) BENZOIC ACID ETHYL ESTER | 1.2 | 1.2 | 1.2 | 1.2 | 1.2 | 1.2 | 1.2 |
| 2,6-DI-TERT-BUTYL-p-CRESOL | 0.20 | 0.20 | 0.20 | 0.20 | 0.20 | 0.20 | 0.20 |
| LUCIRIN TPO | 0.10 | 0.10 | 0.10 | 0.10 | 0.10 | 0.10 | 0.10 |
| CAMPHORQUINONE | 0.5 | 0.5 | 0.2 | 0.2 | 0.2 | 0.2 | 0.5 |
| VANADYL ACETYL-ACETONATE | 0.04 | 0.02 |  |  |  |  |  |
| VANADIUM ACETYL-ACETONATE |  |  | 0.04 |  |  |  |  |
| VANADYL STEARATE |  |  |  | 0.04 |  |  |  |
| TOTAL | 102.04 | 102.02 | 101.70 | 101.70 | 101.70 | 101.70 | 102.00 |
| PASTE | | | | | | | |
| LIQUID | 26 | 26 | 25 | 25 | 25 | 26 | 26 |
| HYDROPHOBIC SILICA | 71 | 71 | 74 | 74 | 74 | 71 | 71 |
| AEROSIL OX-50 | 3 | 3 |  |  |  | 3 | 3 |
| AEROSIL A200 |  |  | 1 | 1 | 1 |  |  |
| TOTAL | 100 | 100 | 100 | 100 | 100 | 100 | 100 |
| EVALUATION RESULT | | | | | | | |
| BENDING STRENGTH [MPa] | 181 | 176 | 188 | 189 | 180 | 188 | 167 |
| ELASTIC MODULUS [GPa] | 10.9 | 10.6 | 10.7 | 10.8 | 9.9 | 9.3 | 9.8 |
| EXTRUSION HARDNESS [N] | 9.3 | 10.2 | 20.1 | 20.4 | 14.7 | 9.6 | 9.6 |

As can be appreciated from Tables 1 and 2, the bending strength and the elastic modulus of the set products of the paste samples of Examples 1 to 10 are desirably high and the extrusion hardness of these paste samples is desirably low.

In contrast, because the paste samples of Comparative Examples 1 to 3 do not contain a vanadium compound, the elastic modulus of the set products of these paste samples is comparatively lower.

In the following, results of measuring the amount of radicals generated during the setting time of the paste samples of Example 4 and Comparative Example 1 will be described.

<Amount of Radicals Generated During Setting Time>

Using the G-Light Prima (manufactured by GC Corporation), light was irradiated onto a specified amount of each paste sample for 20 seconds, and the amount of methacrylic radicals generated 5 minutes thereafter was measured using an electron spin resonance apparatus (manufactured by JEOL Ltd.) as the amount of radicals generated during the setting time of the paste sample. Note that the amount of methacrylic radicals generated is expressed as a peak intensity ratio (relative value) relative to the intensity of a manganese marker 800 as the internal standard in the sample.

The measurement results of the amount of radicals generated during the setting time of the paste samples are indicated in Table 3.

TABLE 3

| | AMOUNT OF RADICALS GENERATED DURING SETTING TIME |
|---|---|
| EXAMPLE 4 | 5.723 |
| COMPARATIVE EXAMPLE 1 | 4.671 |

As can be appreciated from Table 3, a larger amount of radicals are generated during the setting time of the paste sample of Example 4 as compared with the amount of radicals generated in the paste sample of Comparative Example 1.

Although the present invention has been described above with respect to certain illustrative embodiments and examples, the present invention is not limited to the above-described embodiments and examples and various variations and modifications may be made without departing from the scope of the present invention.

What is claimed is:

1. A single-component dental photopolymerizable composition comprising:
   a (meth)acrylate compound, a vanadium compound, an α-diketone compound, a tertiary aromatic amine compound, and a photopolymerization initiator,
   wherein the dental photopolymerizable composition does not include a (meth)acrylate compound having an acid group, and does not include an organic filler, but includes an inorganic filler, and
   wherein the dental photopolymerizable composition does not include an aryl borate compound.

2. The single-component dental photopolymerizable composition according to claim 1, wherein a content of the vanadium compound in the single-component dental photopolymerizable composition is greater than or equal to 0.001 mass % and less than or equal to 1 mass %.

3. The single-component dental photopolymerizable composition according to claim 1, wherein the single-component dental photopolymerizable composition is used as a composite resin for abutment construction.

4. The single-component dental photopolymerizable composition according to claim 1,
   wherein the vanadium compound includes at least one of vanadium acetylacetonate, vanadyl acetylacetonate, and vanadyl stearate, and
   wherein a content of the at least one of vanadium acetylacetonate, vanadyl acetylacetonate, and vanadyl stearate is greater than or equal to 0.02% by mass and less than or equal to 0.20% by mass with respect to 100% by mass of the (meth)acrylate compound.

5. The single-component dental photopolymerizable composition according to claim 1,
   wherein the dental photopolymerizable composition is a paste, and
   wherein a bending strength of a set product of the paste is greater than or equal to 170 MPa.

6. The single-component dental photopolymerizable composition according to claim 1,
   wherein the dental photopolymerizable composition is a paste, and
   wherein a bending elastic modulus of a set product of the paste is greater than or equal to 10 GPa.

7. The single-component dental photopolymerizable composition according to claim 1,
   wherein the dental photopolymerizable composition is a paste, and
   wherein an extrusion hardness of the paste is less than or equal to 20.5 kgf.

8. A single-component dental photopolymerizable composition consisting of:
   a (meth)acrylate compound consisting of one or more kinds of (meth)acrylate not having an acid group;
   one or more vanadium compounds;
   an α-diketone compound;
   a tertiary aromatic amine compound;
   a filler consisting of an inorganic filler;
   a polymerization inhibitor; and
   a photopolymerization initiator.

9. The single-component dental photopolymerizable composition according to claim 1, wherein the dental photopolymerizable composition does not include an acidic compound.

* * * * *